United States Patent [19]

Rocher et al.

[11] Patent Number: 5,547,676
[45] Date of Patent: Aug. 20, 1996

[54] COSMETIC PRODUCT HAVING A STABILIZED REDOX POTENTIAL

[75] Inventors: Daniel Rocher, Les Milles; Hugues Noel, St Chamas, both of France

[73] Assignee: Daniel Jouvance, Aix Les Milles Cedex, France

[21] Appl. No.: 135,475

[22] Filed: Oct. 13, 1993

[30] Foreign Application Priority Data

Oct. 26, 1992 [FR] France ................... 92 12745

[51] Int. Cl.$^6$ ............... A61K 7/48; A61K 33/24
[52] U.S. Cl. ............ 424/401; 424/59; 424/489; 424/617; 424/630; 424/641; 424/642; 424/646; 424/647; 424/648; 424/721; 424/DIG. 6; 514/844
[58] Field of Search ............ 424/59, 401, 489, 424/617, 630, 641, 642, 646, 647, 648, 721, DIG. 6; 514/844

[56] References Cited

U.S. PATENT DOCUMENTS 5,368,610  11/1994  Chan et al. .................. 8/406

FOREIGN PATENT DOCUMENTS 0326143  8/1989  European Pat. Off. .
1247588  10/1960  France .
1352217  1/1964  France .

OTHER PUBLICATIONS

Principles of Dairy Chemistry pp. 233–234 (1959) by R. Jeness & S. Patton.

Primary Examiner—Jyothsna Venkat
Attorney, Agent, or Firm—Young & Thompson

[57] ABSTRACT

Cosmetic product having a stabilized redox potential, comprising, in contact with one another, a cosmetic composition comprising, in an aqueous medium, a water-soluble metal salt, and the metal corresponding to this water-soluble metal salt. The stability of the redox potential of the cosmetic product of the present invention enables the properties of the cosmetic composition, in particular the physiological properties, to be exceptionally well preserved.

8 Claims, No Drawings

COSMETIC PRODUCT HAVING A STABILIZED REDOX POTENTIAL

FIELD OF THE INVENTION

The present invention relates to a cosmetic product having a stabilized redox potential, comprising a metal salt and the corresponding metal.

BACKGROUND OF THE INVENTION

The incorporation solely of metal salts in cosmetic compositions has been known and used for a long time. The addition solely of metals for decorative purposes or for a physiological action (screen, reflector) has also been described. However, the Applicant has not found any description of a simultaneous incorporation of metal salt and its corresponding metal in the prior art in the field of cosmetic products.

SUMMARY OF THE INVENTION

The object of the present invention is to provide a cosmetic product having a stabilized redox potential as a result of bringing a cosmetic composition comprising a water-soluble metal salt in an aqueous medium and the metal corresponding to the water-soluble metal salt into contact with one another.

The cosmetic composition can be any conventional cosmetic composition containing a metal salt and comprising an aqueous or aqueous-alcoholic cosmetic base.

In the present invention, metal salt denotes both a simple salt of a metal and a metal complex. As examples of metal complexes, those formed with a product selected from ammonia solution, EDTA (ethylenediamine tetraacetic acid), HEDTA (hydroxyethyl ethylenediamine triacetic acid), DTPA (diethylenetriamine pentaacetic acid), orotic acid, uric acid, phytic acid, etidronic acid and/or their salts may be mentioned.

The metal of the metal salt can be selected from the group consisting of, in particular, zinc, copper, iron, molybdenum, vanadium, selenium, nickel, manganese and titanium.

The metallic constituent used in combination with the cosmetic composition, according to the present invention, can be in the form of powder and/or granulate dispersed in the cosmetic composition. It can also be in the form of wire, for example a wire attached to the device for sealing the container of the cosmetic product of the present invention, or in the form of a metal component that makes it possible, in particular, to apply the cosmetic composition of the present invention to the skin and/or the dermoskeleton, it being possible for this component to be moulded, extruded or sintered, attached or otherwise to be a part of the container of the cosmetic product. The container of the cosmetic product can, moreover, also be made of the metal or of an alloy of the metal whose salt is incorporated in the cosmetic composition.

The stability of the redox potential of the cosmetic product of the present invention enables, for example, the properties of the cosmetic composition, in particular the physiological properties, to be exceptionally well preserved.

Preferred metals of the present invention are, generally, those whose ionized forms, complexed or otherwise, exhibit physiological activity (for example in combination in metalloenzymes, metalloproteins, haems), that is to say those which are selected from the group consisting of, in particular, zinc, copper, iron, molybdenum, vanadium, selenium, nickel and manganese. From the standpoint of protection against oxidation, however, metals such as zinc, vanadium and titanium are preferred. The preferred proportion of metal salt, expressed as metal, in the composition is between 10 ppm and 1%.

DETAILED DESCRIPTION OF THE INVENTION

Two examples of cosmetic products according to the present invention will be found below.

| ANTIWRINKLE SKIN-CARE CREAM | | |
|---|---|---|
| Demineralized water | qs | 100 |
| Zinc pyrrolidonecarboxylate | | 1.00 |
| Glycerol | | 1.00 |
| 1,3-Butanediol | | 5.00 |
| Sodium lactate | | 0.50 |
| Sodium cetyl sulphate | | 2.50 |
| Preservative | | qs |
| Isoamyl para-methoxycinnamate | | 2.00 |
| Gamma oryzanol | | 1.00 |
| Ethylhexyl laurate | | 17.00 |
| Pentaerythritol stearate | | 3.00 |
| 1,2-propanediol diethylhexanoate | | 6.50 |
| Liquid paraffin | | 8.00 |
| Jojoba oil | | 2.00 |
| PEG 20 Stearate | | 0.75 |
| Glyceryl monolinoleate | | 1.30 |
| Sorbitan monostearate | | 1.50 |
| Dodecamethylcyclohexasiloxane | | 4.00 |
| DL-α-Tocopherol | | 0.10 |
| Retinol palmitate | | 0.15 |
| Polyacrylamide | | 0.60 |
| Deoxyribonucleic acid | | 0.30 |
| Collagen (0.3% solution) | | 3.00 |
| Perfume | | qs |

In combination with a pure zinc wire attached to the lid of the pot.

| SUN CREAM | |
|---|---|
| Distilled water | qs |
| 1,2-propanediol | 2.50 |
| Ethoxylated stearic acid, 100 EO | 2.00 |
| Ethoxylated stearic acid, 30 EO | 2.20 |
| Orthophosphoric acid | 0.09 |
| Magnesium sulphate | 0.50 |
| Copper pyrrolidonecarboxylate | 0.20 |
| Sodium hydroxide | 0.74 |
| Phenylbenzimidazolesulphonic acid | 3.00 |
| Decamethylcyclopentasiloxane | 4.00 |
| Hydrogenated coconut oil | 8.00 |
| Sesame oil | 6.00 |
| Pentaerythritol monostearate | 5.00 |
| Ethylhexyl para-methoxycinnamate | 4.00 |
| Glyceryl monostearate | 4.00 |
| Shea butter | 3.00 |
| tert-Butylmethoxydibenzoylmethane | 3.00 |
| Carnauba wax | 2.00 |
| Decyl oleate | 2.00 |
| Preservative | 1.20 |
| Sea water | 4.00 |
| Diginea extract | 1.00 |
| Perfume | 0.30 |

In combination with a pure copper wire.

It is clear that these examples impose no limitation as regards the other possibilities of combination, according to the present invention, of a metal salt with its corresponding metal.

We claim:

1. Cosmetic product having a stabilized redox potential, comprising, in contact with one another, a metal selected from the group consisting of zinc, copper, iron, molybdenum, vanadium, selenium, nickel, manganese and titanium, and a cosmetic composition comprising, in an aqueous medium, a water-soluble salt of said metal.

2. Cosmetic product as claimed in claim 1, wherein the water-soluble salt is a metal complex.

3. Cosmetic product as claimed in claim 2, wherein the metal complex is a complex formed with a product selected from the group consisting of ammonia solution, EDTA, HEDTA, DTPA, orotic acid, uric acid, phytic acid, etidronic acid and salts thereof.

4. Cosmetic product as claimed in claim 1, wherein the proportion of the water-soluble salt, expressed as metal, is between 0.001% and 1%.

5. Cosmetic product as claimed in claim 1, wherein the metal is in the form of powder dispersed in the cosmetic composition.

6. Cosmetic product as claimed in claim 1, wherein the metal is in the form of granulate dispersed in the cosmetic composition.

7. Cosmetic product as claimed in claim 1, wherein the metal is a wire attached to a device for sealing the container containing of the cosmetic product.

8. Cosmetic product as claimed in claim 1, wherein the metal constitutes a part of a container containing the cosmetic product.

* * * * *